Figure 1:
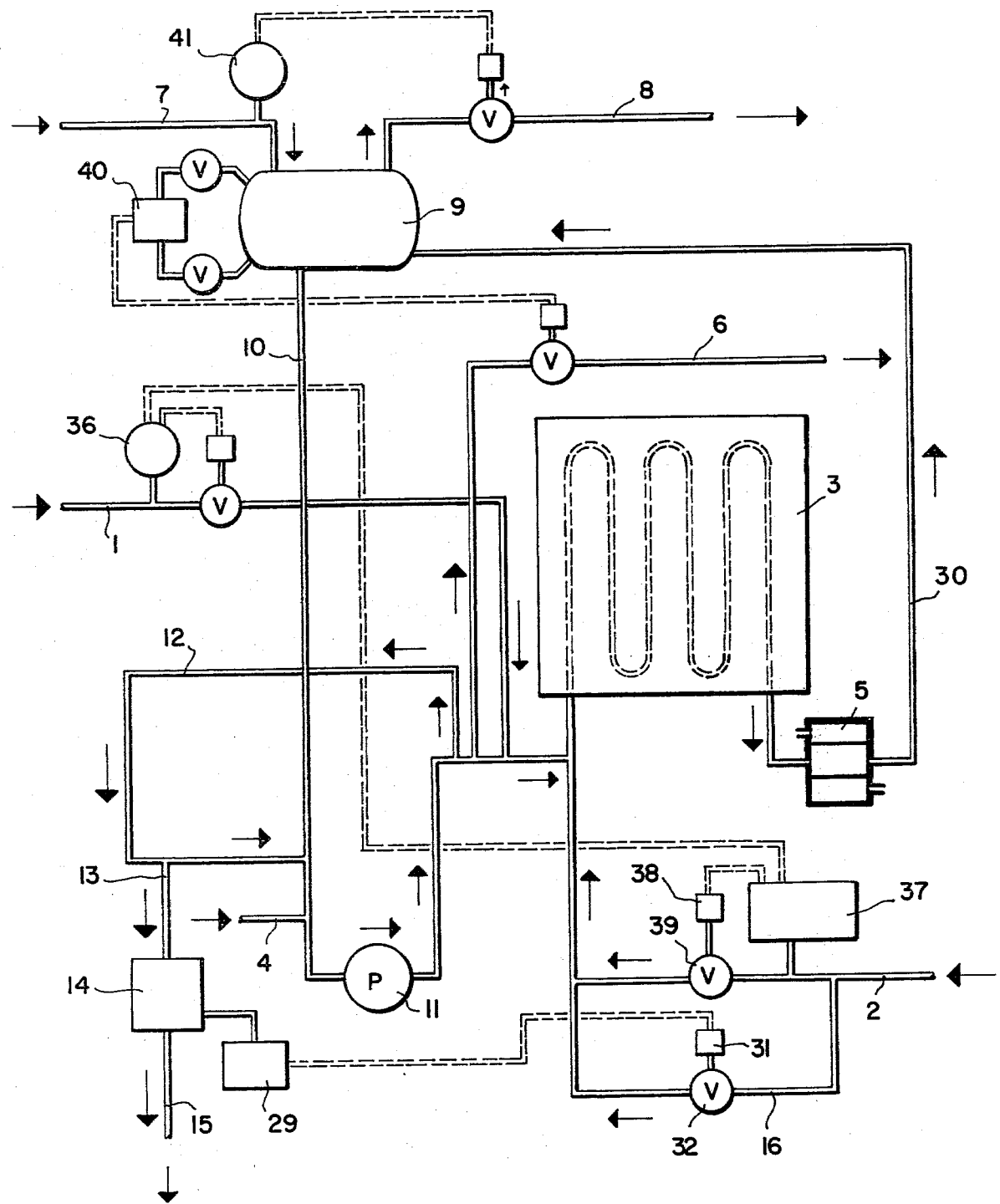

United States Patent [19]

Schmidhammer et al.

[11] 4,259,264
[45] Mar. 31, 1981

[54] PROCESS FOR THE CONTINUOUS CHLORINATION OF OLEFINS IN THE LIQUID PHASE AND AN APPARATUS FOR CARRYING OUT THE PROCESS

[75] Inventors: Ludwig Schmidhammer; Ernst Selbertinger, both of Marktl, Fed. Rep. of Germany

[73] Assignee: Wacker-Chemie GmbH, Munich, Fed. Rep. of Germany

[21] Appl. No.: 3,341

[22] Filed: Jan. 15, 1979

[30] Foreign Application Priority Data

Jan. 26, 1978 [DE] Fed. Rep. of Germany ....... 2803285

[51] Int. Cl.$^3$ .................. C07C 17/02; C07C 17/10
[52] U.S. Cl. .................................................. 570/247
[58] Field of Search ............ 260/660; 204/1 B, 195 R

[56] References Cited

U.S. PATENT DOCUMENTS

| 2,370,871 | 3/1945 | Marks | 204/1 B |
|---|---|---|---|
| 2,382,734 | 8/1945 | Marks | 204/1 B |
| 2,393,367 | 1/1946 | Hammond | 260/660 |
| 2,585,811 | 2/1952 | Marks | 204/1 B |
| 2,758,079 | 8/1956 | Eckfeldt | 204/1 B X |
| 2,914,577 | 11/1959 | Clapp et al. | 260/660 |
| 3,740,326 | 6/1973 | Grubb | 204/1 B X |
| 4,057,478 | 11/1977 | Bruckenstein | 204/195 R |
| 4,172,099 | 10/1979 | Severino | 260/660 |

FOREIGN PATENT DOCUMENTS 732249  4/1966  Canada ..................... 260/660

*Primary Examiner*—Helen M. S. Sneed
*Attorney, Agent, or Firm*—Burgess, Ryan and Wayne

[57] ABSTRACT

In the chlorination of ethylene in the liquid phase, an excess stoichiometric amount of chlorine is normally used in order to achieve as complete as possible a conversion of the ethylene. Part of the excess chlorine reacts by substitution and thereby reduces the yield of desired 1,2-dichloroethane. The unreacted excess chlorine therefore has laboriously to be removed in subsequent reaction steps. As a result of the method according to the invention to limit the chlorine excess to less than 600 ppm by weight in the reaction cycle, these disadvantages can be obviated. The constant compliance with such a low chlorine excess without fluctuations is rendered possible in industrial operation by the arrangement according to the invention for the continuous recording of the chlorine concentration, even in the presence of catalysts.

7 Claims, 3 Drawing Figures

PROCESS FOR THE CONTINUOUS CHLORINATION OF OLEFINS IN THE LIQUID PHASE AND AN APPARATUS FOR CARRYING OUT THE PROCESS

This invention relates to a process for the continuous chlorination of olefins, and particularly for the continuous chlorination of ethylene in the liquid phase in the presence of a chlorination catalyst.

In this process, the reaction mixture is pumped continuously around a circulatory system, through a reaction zone heated to temperatures ranging from 20° to 60° C., and through a heat exchanger to dissipate the heat of reaction. Fresh ethylene, chlorine and chlorination catalyst are admitted to the circulatory system in proportion as crude 1,2-dichloroethane which contains catalyst is removed from the circulatory system.

Such processes are disclosed, for example, in DE-OS Nos. 16 18 273, DE-OS 22 53 730, DE-AS 11 57 592, 15 68 298, 16 68 850 and 17 68 367 and in DE-PS 15 43 108. Ordinarily, the chlorinated hydrocarbon that is obtained is itself used as the solvent. Iron(III) chloride, copper(II) chloride, bismuth(III) chloride, tellurium(IV) chloride and tin(IV) chloride are mentioned as examples of known chlorination catalysts.

In prior art large-scale operations, it is possible to adjust the ratio of ethylene and chlorine relatively approximately, only by means of a ratio-controlling means. Excess chlorine has on the one hand proved advantageous in order to inhibit the formation of carbon-rich resin products and to prevent ethylene passing into the waste gas, but, on the other hand, the reaction yield, relative to chlorine, is impaired, and the number of chlorine substitution reactions increases as the chlorine concentration increases. The purification of the chlorine-containing waste water from the catalyst washings is complicated.

There has been no lack of attempts to influence the chlorine concentration retroactively by determining the chlorine concentration in the reaction cycle. These range from wet-chemistry manual analysis to physical measuring methods. All well known processes, however, have the disadvantages that analysis samples have to be taken and that the purification of the analysis sample is protracted. Even when the measured values ascertained were made available for the control of the ethylene/chlorine ratio in the quickest possible manner, there were undesirable fluctuations in the concentration of dissolved chlorine in the continuous operation. The necessary diverse analysis operations of the conventional processes have a negative influence on the reliability of the measured values ascertained and thus on the control of the reaction.

It was therefore the aim of the invention to find a process for chlorination in which, by means of continuous and reliable recording of the chlorine concentration in the reaction cycle, without protraction, the ratio of ethylene and chlorine can be constantly controlled. Furthermore, it is the aim of the invention so to regulate the chlorine concentration in the reaction cycle that there are no fluctuations, and that, on the one hand, chlorine is in stoichiometric excess relative to the ethylene and, on the other hand, the chlorine excess is only so slight that substitution reactions are suppressed.

The object of the invention is a process for the continuous chlorination of ethylene in the liquid phase in the presence of a chlorination catalyst and with constant circulation of the reaction mixture through a heated reaction zone, in which process chlorine, as the reference variable, and olefin are admitted to the liquid phase continuously in approximately the stoichiometrically necessary ratio, in proportion as the chlorination product is removed from the circulatory system, as a result of presetting a rough ratio and of coordinated precision admittance in doses of ethylene, characterized in that chlorine is present always in a stoichiometric excess of from 50 to 500 ppm by weight, relative to the ethylene, wherein the chlorine concentration in the organic liquid phase is continuously recorded as a proportional electrical signal and passed to a regulator and to a device connected therewith for the precise admittance in doses of the ethylene.

A further object of the invention is a measuring arrangement, as a component part of an apparatus used for the process for the continuous chlorination of ethylene, wherein a continuous electrical signal, proportional to the concentration of dissolved chlorine in the organic phase, is generated, characterized in that a combination of electrodes comprising a measuring electrode and a reference electrode is immersed in the liquid organic phase containing dissolved chlorine.

In an advantageous form of the measuring arrangement, the electrodes are, or the combination of electrodes is, immersed in the organic liquid phase without previously dissolved or suspended catalyst material, which normally has a lower potential than the potential $Cl_2/2Cl^-$, having been removed. A platinum electrode is normally used as the measuring electrode and a calomel electrode is used as the reference electrode. It is especially necessary to maintain a constant pressure of from 10 to 500 mm water column present on the measuring electrolyte solution and the liquid organic phase containing chlorine. In a particularly advantageous manner, a lithium chloride solution containing from 1 to 5 moles/liter is used in the reference electrode.

Surprisingly, the present invention enables the chlorination process to be so analyzed and regulated in the organic liquid phase, in the presence of the catalyst suspension and water concentrations in the organic phase of, in general, less than 25 ppm or, more specifically, even less then 5 ppm, that no fluctuations occur in the concentration of dissolved chlorine during the continuous operation of the chlorinating plant. Using the measuring arrangement according to the invention as a component of an apparatus for carrying out the process, it is possible in chlorinating processes to determine directly and continuously with great reliability the concentration of dissolved chlorine in the liquid organic phase in the presence of the chlorination catalyst. The process according to the invention and the measuring arrangement for the first time enables the chlorination of ethylene in the presence of from 50 to 500 ppm of excess chlorine to be effected with extremely few by-products being formed.

The process according to the invention, and also the measuring arrangement, will be explained with reference to a flow chart (FIG. 1).

Chlorine, as the controlled reference variable, and ethylene, as the ratio-controlled variable, are passed through the conduits 1 and 2, respectively, to conduit 10 and then to the reactor 3 filled with a solvent, such as a chlorinated hydrocarbon, for instance. In the presence of the chlorination catalyst, which is passed through the conduits 4 and 10 to reactor 3, the mixture is heated to the required reaction temperature. Iron(III) chloride, for example, may be used as the chlorination catalyst. The heat of reaction is dissipated in the heat exchanger 5. The reaction mixture is circulated to circulation reservior 9 through conduit 30. Depending on the degree to which the circulation reservoir 9 is filled, chlorinated product that has been produced is removed through the conduit 6. Through the conduit 7, the gas chamber of the circulation reservoir 9 is rinsed with compressed nitrogen, and this rinsing nitrogen and other inert gases, with which the chlorine and the ethylene may possibly have been contaminated, leave the reaction system through the conduit 8 and pass under pressure regulation to the waste gas washing units.

Even though it is possible, in principle, to site the measuring arrangement according to the invention in the flow path of the main product, it is, however, advantageous to arrange a by-pass conduit 12 branching off the circulation conduit 10 on the pressure side of the circulation pump 11, which conduit 12 leads back in to the flow conduit 10 of the main product on the suction side of the circulation pump 11. The measuring electrode arrangement can be arranged in the by-pass conduit 12, but preferably a further bleed conduit 13 in turn branches off the by-pass conduit 12. This conduit 13, owing to its cross-section being smaller than that of the by-pass conduit, feeds only about 50 liters/hour from the by-pass line 12 to the arrangement 14 for measuring the chlorine concentration. The outflow from the measuring equipment 14 is passed directly to the catalyst washing unit from conduit 15.

The electrical signal generated in the chlorine concentration-measuring arrangement 14 is an electrical potential proportional to the chlorine concentration and is converted to an electric current corresponding to the chemical potential (normally between 0 and 20 mA) (see FIG. 3), and, via a regulator 31 and an associated precision control valve 32 in conduit 16, thereby additionally admits proportional amounts of ethylene into the main ethylene admission conduit 2.

In this manner, fluctuations in the ratio of chlorine to ethylene, which may occur in the approximated ratio control process, may be compensated for by the precision control, and the specified desired value of free excess chlorine in the circulating liquid can be held constant.

Figure 2:
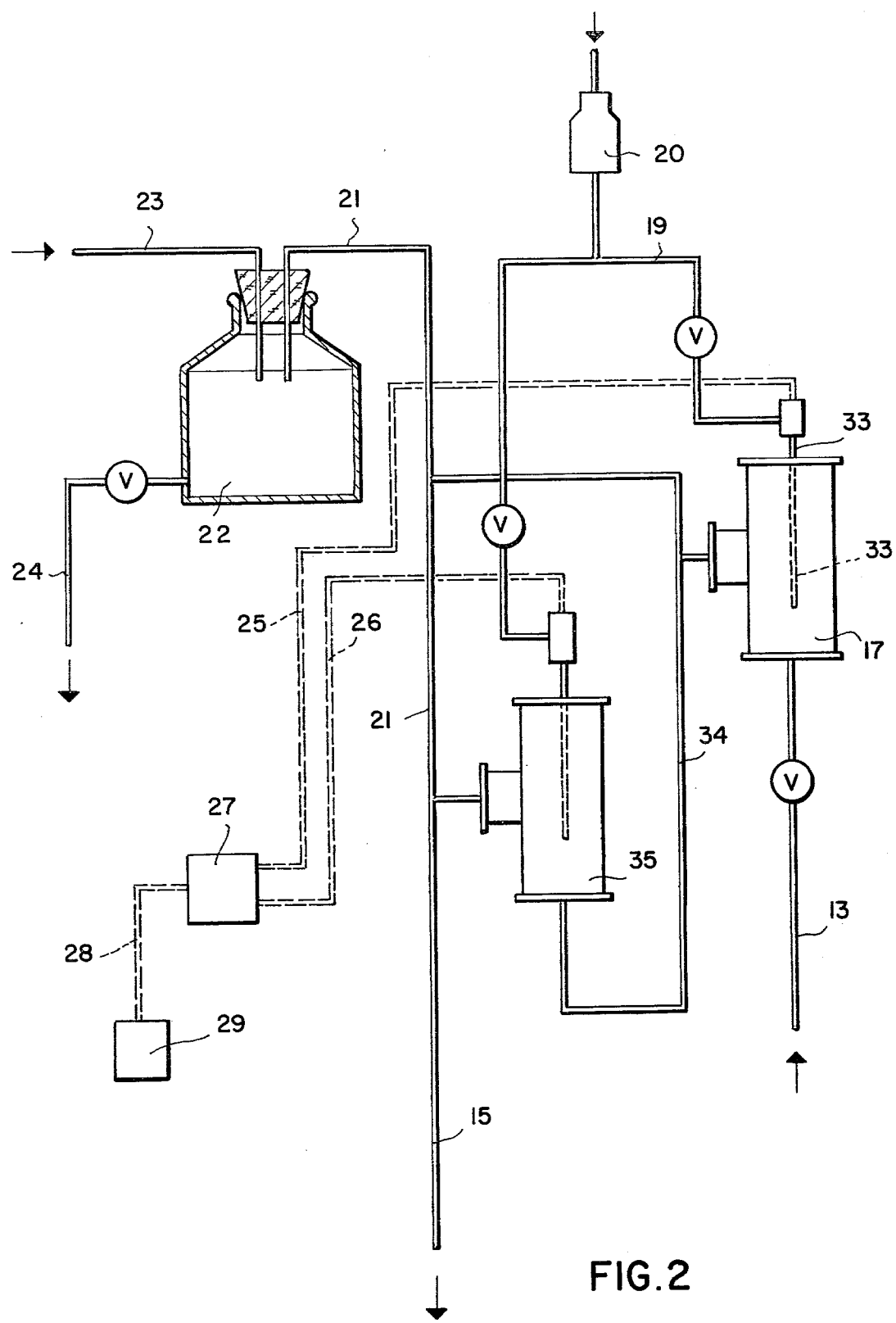

A possible arrangement for the apparatus 14 for measuring the chlorine concentration is shown in FIG. 2. So that fluctuations in the chlorine excess in the main flow conduit do not have to be tolerated in the event of possible disruptions during the potential-measuring operation, the flow meter 17, together with the electrode combination 33, is installed in duplicate with appropriate commutation, although the reliability of the measuring arrangement according to the invention would easily permit a single construction. Through the conduit 13, approximately 50 liters/hour of circulating liquid flow into the flow meter 17 which may be manufactured, for example, from soft soda glass. The electrode combination is located in the flow meter.

A combination of measuring and reference electrodes is used as the electrode. A platinum electrode, for example, is suitable as the reference electrode and a calomel electrode, for example, as the measuring electrode. The electrodes may also be combined to form a single-rod measuring chain. Such electrodes or combinations are commercially available. It has proved an advantage to use a lithium chloride solution having a concentration between 1 and 5 moles of lithium/liter of water as the inner electrolyte of the measuring electrodes. This step substantially prevents the encrustation of the glass membranes of the measuring electrodes when suspended substances, such as catalyst, for example, are present.

The circulating liquid passes from flow meter 17 through the conduit 34 into the second flow meter 35 provided for back-up purposes, and from thence into the open discharge conduit 15 to the catalyst washing unit. To maintain a constant pressure in the flow meter, a pressure compensation is applied thereto via the conduit 21 using a gas buffer that is supplied with a constant flow of nitrogen gas of, for example, 30 mbar.

Referring to FIG. 2, the nitrogen supplying constant pressure which is stored in flow meter 17, enters the system through conduit 23 and is stored in pressure equalization for reservoir 22. An outlet pipe 24 is provided for a nitrogen purge.

Reservoir 20 is provided as a reservoir for the lithium chloride electrolyte which is used as the inner electrolyte of the measuring electrodes. The reservoir is connected with the electrodes through conduit 19.

Figure 3:
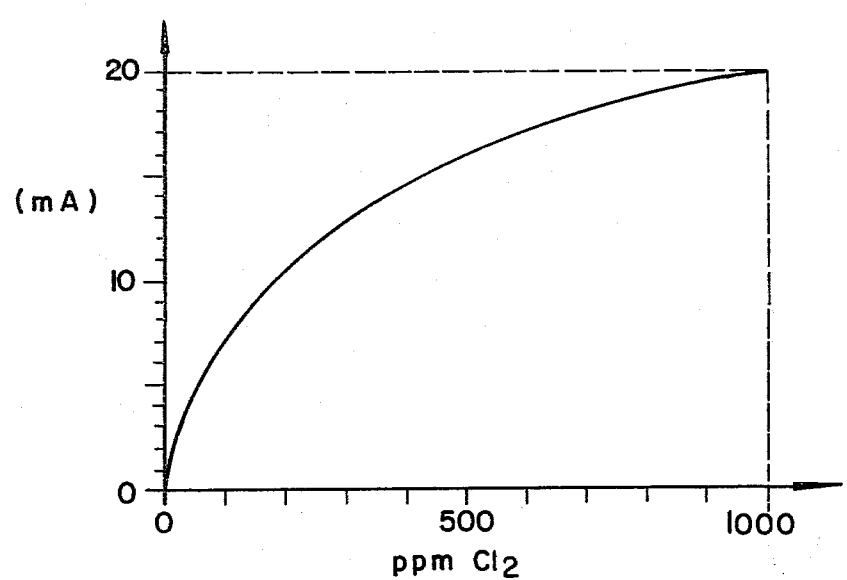

The measured chlorine-redox potential is transferred through the screen measuring lines 25 and 26 to a measuring apparatus, for example a pH-meter 27. The measuring signal is passed, via the line 28, to the regulator 29 which admits the components to be chlorinated into the conduit 2 (FIG. 1) in a precisely controlled manner through its associated precision control valve 32. The electrical potential established in the measuring arrangement is converted in a potential amplifier into a proportional electric current which is, in its turn, proportional to the concentration of chlorine in the circulating liquid. A typical calibration curve that adjusts the output current of a potential amplifier using the chlorine concentration is shown in FIG. 3. In general, chlorine concentrations of between 1 and 2000 ppm may occur, but advantageously the chlorine concentration is set to a value between 50 and 500 ppm, and in particular operation is carried out with concentrations of free chlorine of between 150 and 300 ppm by weight. A precise control of the concentration of free chlorine of between 200 and 250 ppm is easily possible according to the invention and is used in special cases to avoid the occurrence of chlorine substitution reactions.

The following example serves to illustrate the process:

700 m³/h of 1,2-dichloroethane, with 250 ppm of iron(III) chloride as the chlorination catalyst, enter at conduit 4 into conduit 10, are conveyed as the solvent with the assistance of the pump 11 in the circulatory system through the reactor 3 having a total capacity of 16 m³, the heat exchanger 5, the reservoir 9, and the circulatory conduit 30. 3000 Nm³/h (measured at normal temperature and pressure) of liquid chlorine are admitted through conduit 1. In dependence on the flow rate of the chlorine, measured at flow rate control 36, 2900 Nm³/h (measured at normal temperature and pressure) of ethylene are introduced into the reaction system through conduit 2 via the ratio control device 37 and associated regulator 38 and valve 39. The temperature in the reactor 3 is maintained at 40° to 50° C. The heat of reaction generated is dissipated in the heat exchanger 5.

Approximately 1000 liters/h of circulating liquid pass through the analysis ring conduit 12, of which 50 liters/h are continuously tested by the analyzer 14 for the content of free chlorine. The desired value of excess free chlorine is set at regulator 29 to 220 ppm by weight. This desired value is held by the automatic addition of, on average, approximately 50 Nm³/h (measured at normal temperature and pressure) of ethylene via the precision control valve 32 in conduit 16. The resulting 1,2-dichloroethane is drawn off through conduit 6 in dependence on the level control 40 in the circulation reservoir 9, and fed to the catalyst washing unit. It contains 250 ppm of FeCl₃, 300 ppm of HCl, 220 ppm of chlorine, and less than 10 ppm of ethylene.

The waste gases leave the reaction system under pressure control 41 via conduit 8, together with the stream of rinsing nitrogen passed through conduit 7, towards the waste gas washing unit. This stream of waste gas contains, in addition to nitrogen, approximately 0.03% by volume of ethane (contained in the ethylene) and less than 100 ppm by volume of ethylene. The ethylene conversion, relative to the amount of ethylene used, is therefore 99.99%, and the yield relative to ethylene is about 99.7%. The accumulation of by-products, such as ethyl chloride and 1,1,2-trichloroethane and also polymerization product, reaches a total of 0.4% by weight, relative to the crude dichloroethane produced.

Of course, the method according to the invention of detecting chlorine can easily be applied to other chlorination reactions, in which it is necessary to adhere exactly to a chlorine excess to optimize the process, or in which, when chlorination has been completed, the chlorine excess has to be removed again in the most economical manner possible by adding chlorine acceptors prior to the further working up of the chlorination product to prevent side reactions, this addition being controlled in dependence on the measured value of the chlorine.

According to DE-AS No. 1 157 592, when preparing 1,2-dichloroethane a chloride excess of from 0.1 to 10%, preferably of from 2 to 5%, is used in the main reactor, but to reduce the substituting further chlorination of dichloroethane the excess chlorine has to be reacted out in an adjoining reaction operated under pressure with ethylene in excess, wherein the ethylene stream used for this purpose is reacted in the main reactor with the chlorine excess after being passed through the adjoining reactor.

The following comparison example illustrates the extent to which by-products are formed as a result of substitution reactions with a chlorine excess of 0.12%: 700 m³/h of 1,2-dichloroethane, with 250 ppm of iron-(III) chloride as the chlorination catalyst, are guided as the solvent in the circulatory system with the assistance of the pump 11 through the reactor 3, the heat-exchanger 5, cycle conduit 30, the reservoir 9 having a total capacity of 16 m³ and the cycle conduit 10. 3000 Nm³/h (measured at normal temperature and pressure) of liquid chlorine are admitted through conduit 1. By means of the ratio control means 37, 3720 Nm³/h (measured at normal temperature and pressure) of ethylene are introduced into the reaction system through the conduit 2. The temperature in the reactor 3 is held at 40° to 50° C. The reaction heat generated is dissipated in the heat exchanger 5.

The resulting 1,2-dichloroethane is drawn off in dependence on the controlled level 40 in the circulation reservoir 9 through conduit 6 and fed to the catalyst washing unit. It contains 250 ppm of FeCl₃, 1800 ppm of HCl, 1200 ppm of chlorine, and less than 10 ppm of ethylene.

The waste gases leave the reaction system under pressure control 41 through conduit 8, together with the current of rinsing nitrogen of approximately 10 m³/h passed through conduit 7, towards the waste gas washing unit. This current of waste gas contains, in addition to nitrogen, approximately 0.03% by volume of ethane (contained in the ethylene) and less than 100 ppm by volume of ethylene. The ethylene conversion rate, relative to the amount of ethylene used, is thus 99.99%, and the yield relative to ethylene is about 99.7%. The accumulation of by-products, such as ethyl chloride, 1,1,2-trichloroethane, tetrachloroethane and polymerization product amounts to a total of 1.0% by weight, relative to the crude dichloroethane produced.

What is claimed is:

1. In a process for the continuous chlorination of olefins in the liquid phase in the presence of a chlorination catalyst, comprising continuously circulating the reaction mixture through a circulatory system which comprises a heated reaction zone, a heat exchanger to cool said reaction mixture, an outlet conduit, a circulation reservoir, and an inlet conduit; continuously introducing olefin to said inlet conduit; continuously introducing chlorine to said inlet conduit; continuously introducing catalyst to said inlet conduit; and continuously removing the reaction product from said system; the improvement comprising: continuously measuring the concentration of dissolved chlorine in said reaction mixture in a measuring zone, generating an electrical signal proportional to the chlorine concentration, and controlling the introduction of said olefin responsive to said signal such that said chlorine is always present in a stoichiometric excess of from 50 to 500 ppm by weight relative to said olefin.

2. The process of claim 1 wherein a portion of the circulating reaction mixture is continuously passed through the measuring zone for measuring the concentration of dissolved chlorine in the reaction mixture.

3. The process of claim 2 wherein the portion of the circulating reaction mixture which is continuously passed through the measuring zone is removed from the inlet conduit at a point before the chlorine and ethylene are introduced into the inlet conduit.

4. The process of claim 3 wherein a stream of the circulating reaction mixture is removed from the inlet conduit before the chlorine and ethylene are introduced into the inlet conduit, a portion of the stream of reaction mixture is continuously passed through the measuring zone and the portion of the stream is returned to the circulating reaction mixture.

5. The process of claim 4 wherein the reaction mixture is passed through a measuring zone having a reference electrode and a measuring electrode for measuring the concentration of dissolved chlorine.

6. The process of claim 5 wherein the measuring electrode is a platinum electrode and the reference electrode is a calomel electrode.

7. The process of claim 1, 2, 3, 4, 5 or 6 wherein the catalyst has a lower potential than the Cl₂/2Cl⁻ potential.

* * * * *